US011324389B2

(12) United States Patent
Do (10) Patent No.: US 11,324,389 B2
(45) Date of Patent: May 10, 2022

(54) ENDOSCOPE HAVING AN ENDOSCOPE HEAD AND AN ALBARRAN LEVER THAT IS ATTACHABLE TO THE ENDOSCOPE HEAD (71) Applicant: HOYA CORPORATION, Tokyo (JP)

(72) Inventor: Anh Minh Do, Munich (DE)

(73) Assignee: HOYA CORPORATION, Tokyo (JP)

( * ) Notice: Subject to any disclaimer, the term of this patent is extended or adjusted under 35 U.S.C. 154(b) by 266 days.

(21) Appl. No.: 16/315,422

(22) PCT Filed: Jan. 17, 2018

(86) PCT No.: PCT/IB2018/000019
§ 371 (c)(1),
(2) Date: Jan. 4, 2019

(87) PCT Pub. No.: WO2018/134670
PCT Pub. Date: Jul. 26, 2018

(65) Prior Publication Data
US 2019/0328214 A1     Oct. 31, 2019

(30) Foreign Application Priority Data
Jan. 18, 2017  (DE) .......................... 102017100868.3

(51) Int. Cl.
*A61B 1/00*     (2006.01)
*A61B 1/018*    (2006.01)
*G02B 23/24*    (2006.01)

(52) U.S. Cl.
CPC ........ *A61B 1/00098* (2013.01); *A61B 1/0011* (2013.01); *A61B 1/00137* (2013.01); *A61B 1/018* (2013.01); *G02B 23/2476* (2013.01)

(58) Field of Classification Search
CPC .............. A61B 1/00098; A61B 1/0011; A61B 1/00137; A61B 1/018; G02B 23/2476
(Continued)

(56) References Cited

U.S. PATENT DOCUMENTS 5,569,157 A   10/1996   Nakazawa et al.
5,674,181 A   10/1997   Iida
(Continued)

FOREIGN PATENT DOCUMENTS

DE     196 27 016 C1      2/1998
DE     10 2016 10533 A1   9/2016
JP     H08-243076 A       9/1996

OTHER PUBLICATIONS

U.S. Appl. No. 16/328,580 to Anh Minh Do, filed Feb. 26, 2019.
(Continued)

*Primary Examiner* — Michael J Carey
*Assistant Examiner* — Christen A. Sharpless
(74) *Attorney, Agent, or Firm* — Greenblum & Bernstein P.L.C.

(57) ABSTRACT

The invention relates to an endoscope having an endoscope head and an Albarran lever that is attachable to the endoscope head. The Albarran lever has the following: a tool guide surface with which a tool that is guidable through a working channel of an endoscope may come into contact, and a detent device for form-fit locking to a force transmission section of the endoscope head of the endoscope that is actuatable from a proximal side of the endoscope, wherein the force transmission section transmits a force to the Albarran lever in order to pivot the Albarran lever.

8 Claims, 6 Drawing Sheets

(58) Field of Classification Search
USPC .......................................................... 600/106
See application file for complete search history.

(56) References Cited

U.S. PATENT DOCUMENTS

| | | | |
|---|---|---|---|
| 5,707,344 A * | 1/1998 | Nakazawa | A61B 1/018 600/125 |
| 2016/0270636 A1* | 9/2016 | Iwasaka | A61B 1/00137 |
| 2018/0249894 A1* | 9/2018 | Koi | A61B 1/018 |

OTHER PUBLICATIONS

International Search Report issued in International Bureau of WIPO Patent Application No. PCT/JP2018/000019, dated Apr. 30, 2018, along with an English translation thereof.

* cited by examiner

ENDOSCOPE HAVING AN ENDOSCOPE HEAD AND AN ALBARRAN LEVER THAT IS ATTACHABLE TO THE ENDOSCOPE HEAD

The present invention relates to an endoscope having an endoscope head and an Albarran lever that is attachable to the endoscope head.

Such an Albarran lever may be used in an endoscope for examining, for example, the esophagus as well as the duodenum, the bile duct, the gall bladder, the pancreatic duct, the pancreas, etc.

Such an endoscope has an optical system (illumination device and camera). At the outlet of the working channel, the endoscope also has the Albarran lever, which by pivoting allows a targeted deflection of the tools that are inserted through the working channel.

The endoscope undergoes treatment after use in order to reliably exclude the transmission of all pathogens or microorganisms such as bacteria, viruses, fungi, worms, and spores. During the treatment, the endoscope is initially manually cleaned to completely remove organic material or chemical residues. Machine disinfection or sterilization takes place after the cleaning. The intent is to prevent pathogens or microorganisms, etc., which have come into contact with the endoscope during use thereof, from being transmitted to the patient during the next use.

For example, DE 196 27 016 C1 discloses an endoscope having an Albarran lever. More precisely, the endoscope has a carrier, detachable from the endoscope, in which the Albarran lever is pivotably situated on an axis supported in the carrier. The pivoting of the Albarran lever takes place via a traction cable that is anchored on the Albarran lever and guided in the endoscope.

The object of the present invention is to provide an endoscope in which pathogens that have come into contact with an endoscope are better prevented from being transmitted to the patient during the next use.

This object is achieved by an endoscope having the features of claim 1. Advantageous refinements are the subject matter of the dependent claims.

In the endoscope according to the invention, an Albarran lever that is attachable to an endoscope head has a tool guide surface with which a tool that is guidable through a working channel of an endoscope may come into contact, and a detent device for form-fit locking to a force transmission section of the endoscope head of the endoscope that is actuatable from a proximal side of the endoscope, wherein the force transmission section transmits a force to the Albarran lever in order to pivot the Albarran lever.

Such an Albarran lever may be easily locked to and detached from the endoscope head. The Albarran lever may thus be designed as a single-use article. Such an Albarran lever may be discarded after a single use and replaced with a fresh Albarran lever. It may thus be ensured that the Albarran lever cannot transmit pathogens when the endoscope is used on the next patient. Of course, the used Albarran lever may also be transferred to cleaning and sterilization.

The detent device may have a geometric shape on the proximal side of the Albarran lever that corresponds to a countershape of a shaft section of the force transmission section of the endoscope head. The Albarran lever is mountable on this shaft section. A locking means of the detent device may prevent the Albarran lever from being removed from the shaft section of the force transmission section of the endoscope head. Thus, the Albarran lever, with a very simple design, may be locked to and detached from the endoscope head. The shape-related locking provides the locked state with sufficient security from unintentional removal of the Albarran lever from the endoscope head.

The locking means may be provided on the side of the Albarran lever opposite from the tool guide surface. Thus, the elements involved with the locking of the Albarran lever do not adversely affect a tool that is guided between a working channel and the tool guide surface.

The locking means may be designed as a locking lever that is provided on the Albarran lever and is movable relative to the Albarran lever. The locking lever may be rotatable with respect to the Albarran lever. The Albarran lever may have a rotary shaft on the side of the Albarran lever opposite from the tool guide surface, the locking lever being rotatable on the rotary shaft relative to the Albarran lever.

Alternatively, the locking means may be designed as a slider that is provided on the Albarran lever and is displaceable relative to the Albarran lever. The slider may be displaceable relative to the Albarran lever.

The locking means may have an actuating device, on the side of the Albarran lever opposite from the tool guide surface, for actuating the locking means. Thus, the locking means is also situated on the Albarran lever in such a way that it does not adversely affect a tool that is guided between a working channel and the tool guide surface. Such an actuating device is usable with a locking lever or a slider.

The Albarran lever may be made of plastic, and is therefore inexpensive and well suited as a single-use part.

On the endoscope head according to the invention, a shaft section of the force transmission section of the endoscope head and the detent device of the Albarran lever may establish a form-fit connection via which the force for pivoting the Albarran lever is transmittable from the endoscope head to the Albarran lever.

The geometric shape of the detent device may form a countershape to the geometric shape of the shaft section of the force transmission section of the endoscope head.

The endoscope may have a cap that is mountable on the outer circumference of the endoscope head from the distal side. The distal section of the endoscope head and the Albarran lever are thus protected by the cap. The cap is separate from a traction cable for actuating the Albarran lever. In the cap that is pushed onto the endoscope head from the distal side, the Albarran lever is then situated so as to be pivotable relative to the cap. The cap has an opening through which microtools may be pushed. The cap is detachably mountable on the distal side of the endoscope head.

The endoscope may be a duodenoscope.

The aspects of the present invention discussed above may be suitably combined.

The present invention is described in greater detail below with reference to the drawings, based on exemplary embodiments.

EXEMPLARY EMBODIMENT 1

A first exemplary embodiment of the present invention is described below with reference to FIGS. 1 through 10.

An endoscope head 1 according to the invention is described first, with reference to FIGS. 1 through 6.

Figure 1:
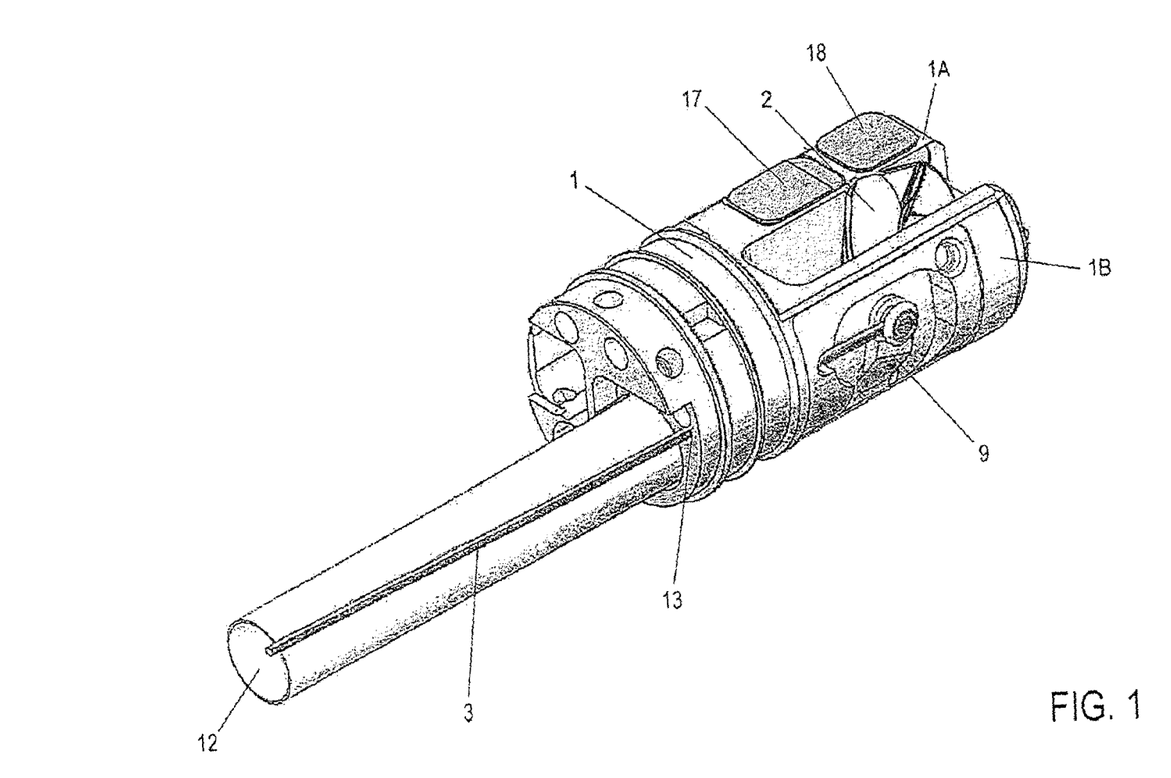
FIG. 1 shows a schematic perspective view of an endoscope head with an Albarran lever in one exemplary embodiment of the present invention.

The endoscope head 1 according to the invention is designed as a cylindrical body, and has a working channel 12 and a traction cable channel 13 that each extend along the longitudinal direction of the endoscope head 1 and parallel to one another. The traction cable channel 13 guides a traction cable 3 for actuating an Albarran lever 2. The working channel 12 guides microtools for examining, for example, the esophagus as well as the duodenum, the bile duct, the gall bladder, the pancreatic duct, the pancreas, etc.

On the distal side, the endoscope head 1 has an optical system extension 1A on which a camera 17 and an illumination device 18 are provided in a known manner; in FIG. 1 this optical system extension is shown on the rear side in the perspective view.

The working channel 12 ends in a section of the endoscope head 1 that is spaced apart from the distal end, where it forms a distal outlet opening of the working channel.

The Albarran lever 2, which can pivot relative to the endoscope head 1, is situated distal from the distal outlet of the working channel 12. The working channel 12 thus extends in the distal direction toward the Albarran lever 2.

On the distal side, the endoscope head 1 has an Albarran lever support extension 1B, shown in FIG. 1 on the front side in the perspective view. A pivot shaft 10 is supported on the Albarran lever support extension 1B in such a way that it protrudes with respect to an inner space between the optical system extension 1A and the Albarran lever support extension 1B. The pivot shaft 10 forms a force transmission section that applies a rotational motion force to the Albarran lever 2. The pivot shaft 10 is the rotary shaft of the Albarran lever 2, in a manner of speaking.

More precisely, the rotational motion force for the Albarran lever 2 is applied by the traction cable 3, whose traction cable nipple is coupled to one end of a lever element 9. The other end of the lever element 9 is connected in one piece to the end of the pivot shaft 10 that is supported in the Albarran lever support extension 1B. The opposite end of the pivot shaft 10 forms a shaft section 11 that protrudes from the Albarran lever support extension 1B toward the optical system extension 1A.

The Albarran lever 2 is mounted on this shaft section 11 of the pivot shaft 10 protruding into the inner space between the optical system extension 1A and the Albarran lever support extension 1B. The shaft section 11 is positioned in such a way that it is opposite from the distal outlet opening of the working channel 12.

The pivot shaft 10 thus has one end that is situated inside the Albarran lever support extension 1B. The traction cable 3 engages over the lever element 9 on the end of the pivot shaft 10 opposite from the shaft section 11. In other words, the distal end of the traction cable 3 is in operative connection with the end of the pivot shaft 10 opposite from the shaft section 11. Pulling the traction cable 3 in the proximal direction thus causes the pivot shaft 10 to rotate.

The end of the pivot shaft 10 opposite from the shaft section 11 is sealed off from the surroundings. The traction cable 3 is situated in the traction cable channel. The traction cable channel is likewise sealed off from the surroundings. The traction cable 3 thus has no contact with the surroundings of the endoscope head 1. A sealed space in which the distal end of the traction cable 3, the lever element 9, and the end of the pivot shaft 10 opposite from the shaft section 11 are situated is provided in the Albarran lever support extension 1B. This sealed space is open only at the proximal side, via the traction cable channel.

The shaft section 11 of the pivot shaft 10 has the shape of a straight prism with a polygon as the base surface in the longitudinal direction of the pivot shaft 10. A triangle or quadrangle, for example, may be selected as the shape of the shaft section 11. In the present exemplary embodiment, the shaft section 11 has the shape of a quadrangle (see FIGS. 3 and 6).

The Albarran lever 2 is described below with reference to FIGS. 7 through 10.

Figure 5:
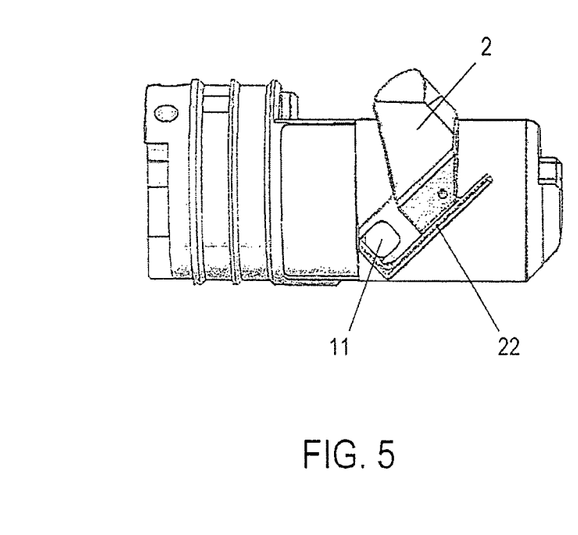
FIG. 5 shows a schematic side view of the endoscope head with the Albarran lever installed.
Figure 6:
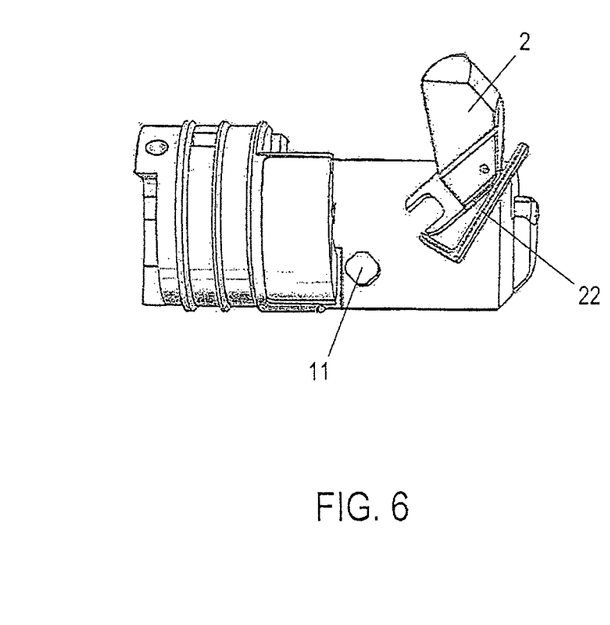
FIG. 6 shows a schematic side view of the endoscope head with the Albarran lever not installed.

On the proximal side, the Albarran lever 2 has an adaptive shape 21 that forms a countershape to the shape of the shaft section 11. For this purpose, the adaptive shape 21 must be able to transmit a rotation of the pivot shaft 10 to the Albarran lever 2. In the present exemplary embodiment, the adaptive shape 21 is quadrangular, as shown in FIG. 5 and in FIGS. 7 through 10.

The Albarran lever 2 is installed on the endoscope head 1 in such a way that the adaptive shape 21 points in the proximal direction. When the Albarran lever 2 is pushed onto the shaft section 11, the adaptive shape 21 encloses the circumferential surface of the shaft section 11 on three sides, for example on the top, on the distal side, and on the bottom.

The Albarran lever 2 has a tool guide surface with which a tool that is guidable through the working channel of the endoscope may come into contact. In the exemplary embodiment, the tool guide surface 20 extends obliquely on the Albarran lever 2; i.e., it is turned toward the proximal side and the upwardly pointing side of the Albarran lever 2 in FIGS. 7 through 10.

A detent tab or locking tab 24 of a locking lever 22 engages with the adaptive shape 21.

The locking lever 22 forms a locking means of the present invention, and together with the adaptive shape 21 forms a detent device of the present invention.

The locking lever 22 is connected to the Albarran lever 2 via a rotary shaft 23. The locking lever 22 may be pivoted relative to the Albarran lever 2 by means of the rotary shaft 23.

Figure 2:
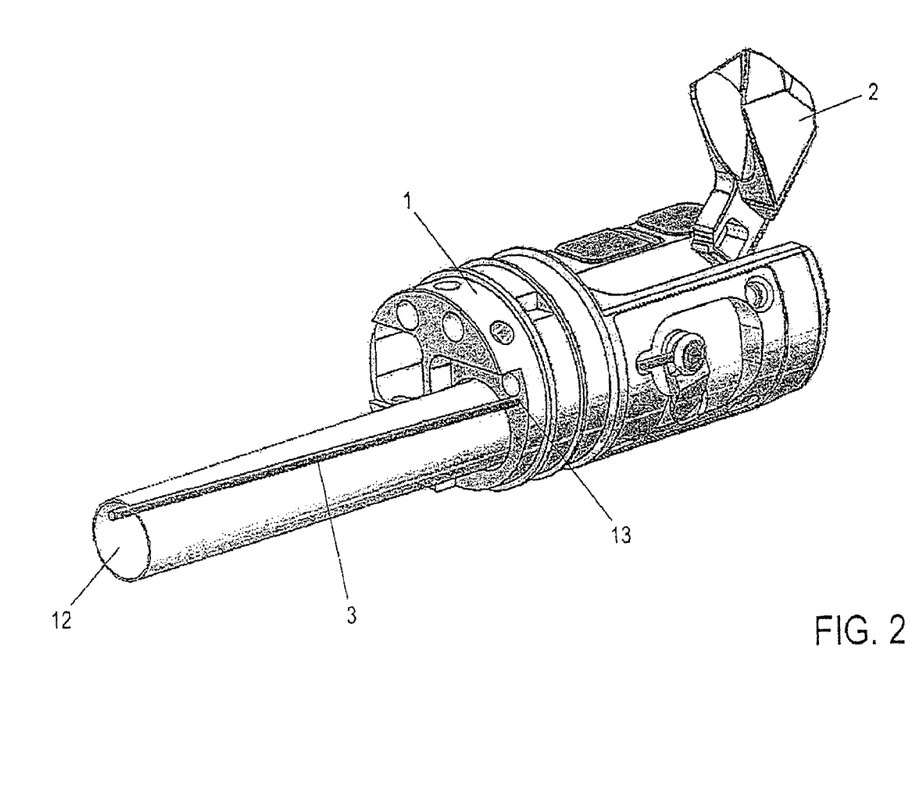
FIG. 2 shows a schematic perspective view of the endoscope head from FIG. 1, with the Albarran lever detached.
Figure 3:
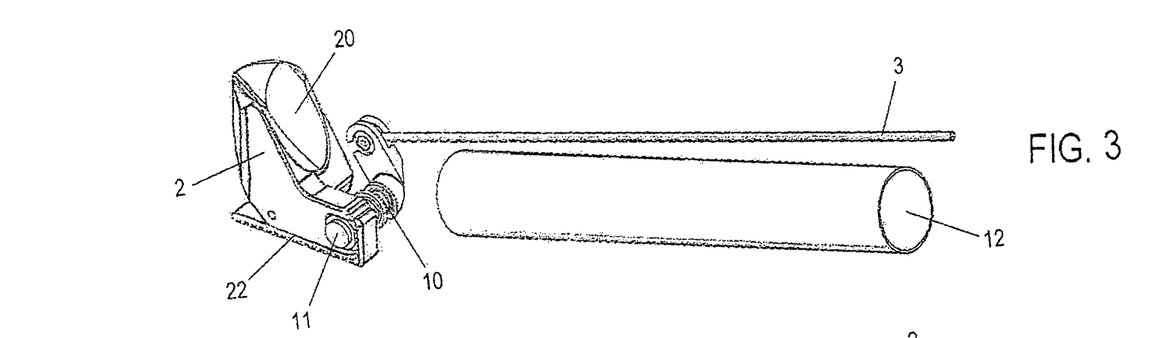
FIG. 3 shows a schematic perspective view of the endoscope head with the Albarran lever from FIG. 1, with the housing of the endoscope head omitted for reasons of clarity.
Figure 4:
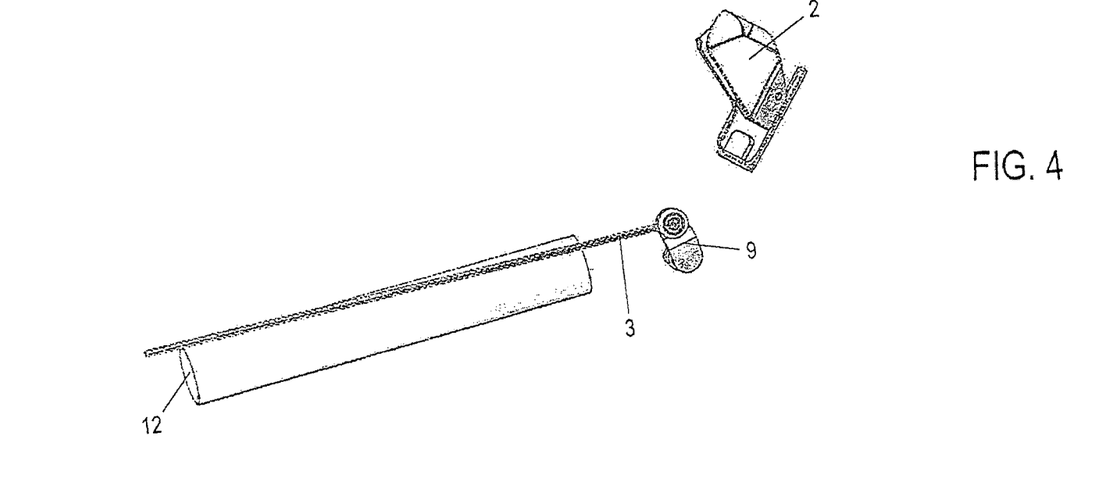
FIG. 4 shows a schematic perspective view similar to FIG. 3, with the Albarran lever detached.
Figure 7:
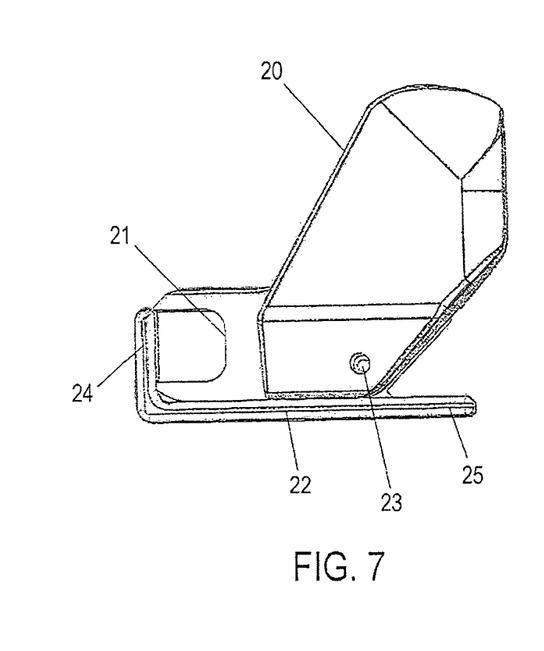
FIG. 7 shows a schematic side view of the Albarran lever in the exemplary embodiment, in a state in which the locking lever is locked.
Figure 8:
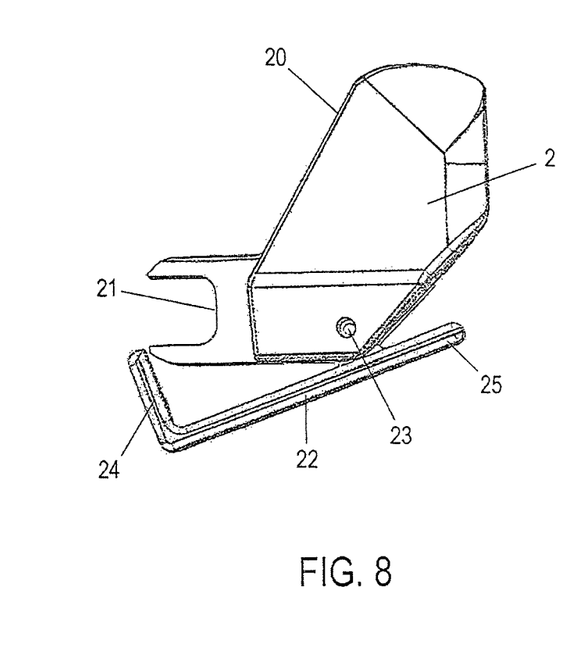
FIG. 8 shows a schematic side view of the Albarran lever in the exemplary embodiment, in a state in which a locking lever is not locked.
Figure 9:
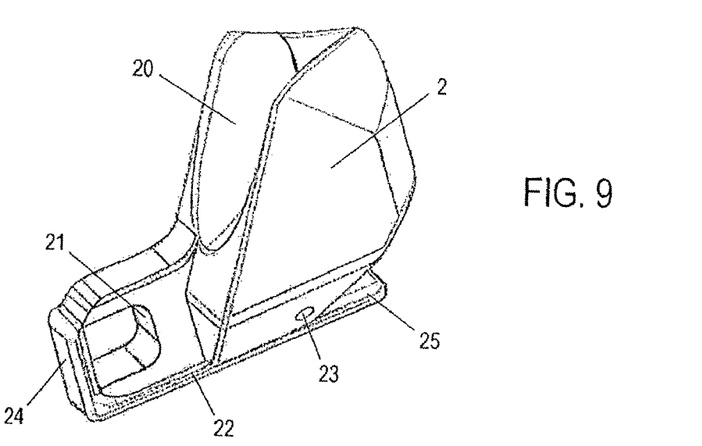
FIG. 9 shows a schematic perspective view of the Albarran lever in the exemplary embodiment, in a state in which the locking lever is locked.
Figure 10:
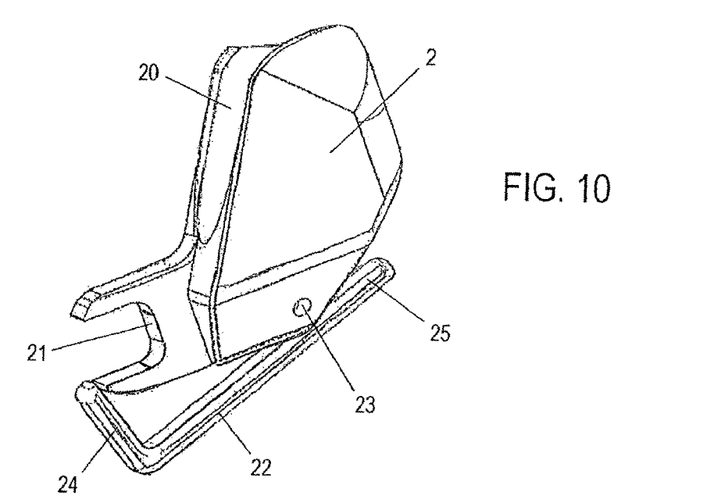
FIG. 10 shows a schematic perspective view of the Albarran lever in the exemplary embodiment, in a state in which a locking lever is not locked.

The locking lever 22 and the rotary shaft 23 are both provided on the side of the Albarran lever 2 opposite from the tool guide surface 20 (i.e., on the bottom side of the Albarran lever 2 in FIG. 2). The distal end of the locking lever 22 forms an actuating device 25. When the distal end of the locking lever 22 is pushed toward the Albarran lever 2, the locking lever 22 pivots in such a way that the detent tab 24 moves away from the adaptive shape 21. When the distal end of the locking lever 22 is moved away from the Albarran lever 2, the locking lever 22 pivots in such a way that the detent tab 24 moves toward the adaptive shape 21. In the latter case, the proximal side of the adaptive shape 21 is closed by the detent tab 24 (see FIG. 7). An urging mechanism, not shown, such as a spring (leaf spring or coil spring) that pretensions the distal section of the locking lever 22 away from the Albarran lever 2, is preferably situated in the area distal from the rotary shaft 23. In other words, pretensioning which closes the detent tab 24 is applied to the locking lever 22. Thus, the adaptive shape 21 is closed by the detent tab 24 when the locking lever 22 is not actuated. FIG. 7 shows the nonactuated state.

Thus, when the Albarran lever 2 is pushed onto the shaft section 11, a distal face of the detent tab 24 rests against a proximal face of the circumferential surface of the shaft section 11.

When the detent tab 24 of the locking lever 22 closes or locks on the adaptive shape 21 in the position that is pushed onto the shaft section 11, the circumferential surface of the shaft section 11 is enclosed by the detent tab 24 and the adaptive shape 21. The distal face of the detent tab 24 prevents the Albarran lever 2 from being pulled off the endoscope head 1 in the distal direction.

The components of the Albarran lever 2 are made of plastic. The Albarran lever 2 may be manufactured from plastic by means of a 3D printer or injection molding, for example. However, the Albarran lever may be manufactured precisely, and yet at low cost, using a 3D printer or injection molding. Other suitable manufacturing methods may be used, provided that they allow precise, cost-effective production.

Function of the Invention

When the Albarran lever 2 according to the invention is mounted on the shaft section 11 of the pivot shaft 10 of the endoscope head 1, the Albarran lever 2 is inserted into the inner space between the optical system extension 1A and the Albarran lever support extension 1B in such a way that the adaptive shape 21 of the Albarran lever 2 points in the proximal direction. The locking lever 22 is opened by pressing the actuating section 25 (see FIGS. 6 and 8), so that the adaptive shape 21 of the Albarran lever 2 may be pushed onto the shaft section 11 of the pivot shaft 10. The locking lever 22 is then closed, whereupon the detent tab 24 is pushed to the proximal side of the shaft section 11 (in FIG. 5, to the left below the shaft section 11) in front of the shaft section 11. The Albarran lever 2 is thus locked to the shaft section 11 of the pivot shaft 10.

When the Albarran lever 2 is situated on the endoscope head 1 as described above, a cap (not shown) may be placed on the distal outer circumference of the endoscope head 1. This cap facilitates the insertion of the endoscope head 1 in the patient. The cap has an opening on the upwardly pointing side in FIG. 1, i.e., on the side at which the microtools are pushed by the Albarran lever 2 and to which the camera 17 and illumination device 18 point.

After the endoscope is inserted, the Albarran lever 2 and the cap are removed. The detent tab 24 is pushed away from the proximal side of the shaft section 11 by pressing the actuating section 25. In this way, the Albarran lever 2 may be pulled off from the shaft section 11 of the pivot shaft 10 in the distal direction. The Albarran lever 2 and the cap may be discarded. Only the endoscope together with the endoscope head 1 are transferred to cleaning and sterilization.

Effects of the Invention

The Albarran lever 2 may be provided as a separate, sterilely packaged module which an operator of the endoscope accesses.

The Albarran lever 2 may be easily installed on and removed from the endoscope head 1. The detent device made up of the locking lever 22 and the adaptive shape 21 establishes a form-fit connection with the shaft section 11 of the pivot shaft 10, via which the force for pivoting the Albarran lever 2 is reliably transmitted from the endoscope head 1 to the Albarran lever 2. A simple, cost-efficient Albarran lever is thus provided which is spatially separate from the traction cable 3. Due to its geometric design, an Albarran lever provides many undercuts to which pathogens, etc., may attach during use, and which may possibly remain on the Albarran lever even after intensive cleaning and sterilization. However, the Albarran lever 2 may be discarded after a single use. Thus, the Albarran lever 2 according to the invention provides the option for preventing pathogens, etc., which have come into contact with the endoscope during use thereof, from being transmitted to the next patient during the next use.

The Albarran lever 2 may be used on existing endoscopes that have a corresponding shaft section 11.

The traction cable channel is separate from the Albarran lever 2. In addition, the traction cable channel is separate from the cap. Thus, the traction cable channel is separate from the elements that are exposed to contamination and have a relatively complex geometry with undercuts, edges, etc. The traction cable channel is sealed off in the endoscope head, with the traction cable being completely sealed off from the surroundings. The seal of the traction cable channel and of the traction cable is watertight. This prevents pathogens from being able to penetrate into the traction cable channel or come into contact with the traction cable.

EXEMPLARY EMBODIMENT 2

In the first exemplary embodiment, the locking lever 22 forms the locking means of the present invention. In the present, second exemplary embodiment (not shown in the drawings), a slider forms the locking means of the present invention.

The adaptive shape 21 is designed in such a way that when the Albarran lever 2 is pushed onto the shaft section 11, the adaptive shape encloses the circumferential surface of the shaft section 11 on three sides, i.e., on the proximal side, on the top, and on the distal side.

Instead of the locking lever 22, the slider is provided on the side of the Albarran lever opposite from the tool guide surface 20. The slider can be pushed in the proximal direction in order to close the bottom side of the adaptive shape 21. The slider can be pushed in the distal direction in order to open the bottom side of the adaptive shape 21.

The Albarran lever in the second exemplary embodiment may also be discarded after use, and provides the same effects and advantages as with the first exemplary embodiment.

Alternatives

The cap 1 mentioned in exemplary embodiment 1 may be omitted.

In one alternative, the locking lever 22 of the first exemplary embodiment, instead of the detent tab 24, may have the shape of a cylindrical pin that may be inserted into a through hole or blind hole in the shaft section 11. In this alternative, the form-fit connection between the shaft section 11 of the force transmission section 10 of the endoscope head and the detent device of the Albarran lever 2 is established by the cylindrical pin on the proximal side of the locking lever 22 and the borehole in the shaft section 11, which is adapted to the shape of the cylindrical pin. In this alternative, the shaft section 11 itself may even have a circular cross section (cylindrical shape).

The invention is usable in a duodenoscope. The principle of the invention may also be applied in an ultrasound endoscope and in any other type of endoscope.

A working channel having an Albarran lever at the end of the working channel is shown in the exemplary embodiments. The invention may also be used in endoscopes that have multiple working channels, each with an Albarran lever at the end of the respective working channel.

The described alternatives may be combined, and may be used in all exemplary embodiments.

REFERENCE SIGNS LIST

1 endoscope head
1A optical system extension
1B Albarran lever support extension
2 Albarran lever
3 traction cable
9 lever element
10 force transmission section of the endoscope head
11 shaft section
13 traction cable channel
17 camera
18 illumination device
20 tool guide surface
21 adaptive shape
22 locking lever
23 rotary shaft
24 detent tab
25 actuating device

The invention claimed is:

1. An endoscope having an endoscope head and an Albarran lever that is attachable to the endoscope head, wherein the Albarran lever comprises:
   a tool guide surface with which a tool that is guidable through a working channel of an endoscope may come into contact;
   a detent for form-fit locking to a pivot shaft of the endoscope head of the endoscope that is actuatable from a proximal side of the endoscope, wherein the pivot shaft transmits a force to the Albarran lever in order to pivot the Albarran lever, the detent comprising:
      a locking lever provided on the Albarran lever and movable relative to the Albarran lever; and
      a geometrically-shaped section on the proximal side of the Albarran lever that corresponds to a shape of a section of the pivot shaft; and
   a rotary shaft extending through a side of the Albarran lever opposite the tool guide surface, wherein
   the locking lever rotates about the rotary shaft relative to the Albarran lever to capture the pivot shaft within the detent and prevents the Albarran lever from being removed from the pivot shaft.

2. The endoscope according to claim 1, wherein the locking lever is provided on a side of the Albarran lever opposite from the tool guide surface.

3. The endoscope according to claim 1, wherein the locking lever has an actuator on a side of the Albarran lever opposite from the tool guide surface, for actuating the locking lever.

4. The endoscope according to claim 1, wherein the Albarran lever is made of plastic.

5. The endoscope according to claim 1, wherein the section of the pivot shaft and the detent of the Albarran lever establish the form-fit connection via which the force for pivoting the Albarran lever is transmittable from the endoscope head to the Albarran lever.

6. The endoscope according to claim 5, wherein a geometric shape of the detent of the Albarran lever forms a countershape to the shape of the shaft section of the pivot shaft.

7. The endoscope according to claim 1, wherein the endoscope has a cap that is mountable on the outer circumference of the endoscope head from the distal side,
   wherein the cap is separate from a traction cable for actuating the Albarran lever.

8. The endoscope according to claim 1, wherein the endoscope is a duodenoscope.

* * * * *